US008834951B2

(12) United States Patent
Harel et al.

(10) Patent No.: US 8,834,951 B2
(45) Date of Patent: Sep. 16, 2014

(54) DRY GLASSY COMPOSITION COMPRISING A BIOACTIVE MATERIAL

(75) Inventors: Moti Harel, Pikesville, MD (US); Roger Drewes, Hockessin, DE (US); January Scarbrough, Silver Spring, MD (US)

(73) Assignee: Advanced Bionutrition Corporation, Columbia, MD (US)

( * ) Notice: Subject to any disclaimer, the term of this patent is extended or adjusted under 35 U.S.C. 154(b) by 0 days.

(21) Appl. No.: 13/378,106

(22) PCT Filed: Jan. 28, 2011

(86) PCT No.: PCT/US2011/022821
§ 371 (c)(1),
(2), (4) Date: Mar. 29, 2012

(87) PCT Pub. No.: WO2011/094469
PCT Pub. Date: Aug. 4, 2011

(65) Prior Publication Data
US 2012/0322663 A1    Dec. 20, 2012

Related U.S. Application Data

(60) Provisional application No. 61/299,315, filed on Jan. 28, 2010.

(51) Int. Cl.
*A23L 2/00*      (2006.01)
*A23L 2/38*      (2006.01)
*A61K 9/16*      (2006.01)
*A61K 9/19*      (2006.01)

(52) U.S. Cl.
CPC ............ *A61K 9/1658* (2013.01); *A61K 9/1623* (2013.01); *A61K 9/19* (2013.01); *A61K 9/1652* (2013.01)
USPC ...... 426/590; 424/93.51; 424/93.4; 424/93.6; 424/93.1; 424/94.1; 424/184.1; 504/358; 514/1.1; 426/531

(58) Field of Classification Search
None
See application file for complete search history.

(56) References Cited

U.S. PATENT DOCUMENTS

| | | | |
|---|---|---|---|
| 3,241,977 A * | 3/1966 | Mitchell et al. ............ | 426/591 |
| 5,262,187 A | 11/1993 | Hahn | |
| 5,766,520 A | 6/1998 | Bronshtein | |
| 6,190,701 B1 | 2/2001 | Roser et al. | |
| 6,306,345 B1 * | 10/2001 | Bronshtein et al. ............ | 422/41 |
| 6,534,087 B2 | 3/2003 | Busson et al. | |
| 6,726,934 B1 | 4/2004 | Prokop | |
| 6,733,759 B2 | 5/2004 | Ivey et al. | |
| 6,884,866 B2 | 4/2005 | Bronshtein et al. | |
| 6,964,771 B1 | 11/2005 | Roser et al. | |
| 7,153,472 B1 | 12/2006 | Bronshtein | |
| 7,381,425 B1 | 6/2008 | Truong-Le | |
| 2004/0241313 A1 | 12/2004 | Nana et al. | |
| 2007/0031534 A1 | 2/2007 | Tsujimoto | |
| 2008/0229609 A1 | 9/2008 | Bronshtein | |
| 2009/0155351 A1 | 6/2009 | Hejl et al. | |
| 2009/0246184 A1 | 10/2009 | Harel et al. | |
| 2010/0015177 A1 * | 1/2010 | Drew ..................... | 424/202.1 |
| 2012/0009248 A1 | 1/2012 | Truong-Le et al. | |

FOREIGN PATENT DOCUMENTS

| | | |
|---|---|---|
| CN | 101287449 A | 10/2008 |
| EP | 471904 A1 * | 2/1992 |
| GB | 1 232 057 A | 5/1971 |
| WO | WO 98/24327 | 6/1998 |
| WO | WO 2005/060937 A1 | 7/2005 |
| WO | WO 2007/038926 A1 | 4/2007 |
| WO | WO 2007/079147 A2 | 7/2007 |
| WO | WO 2010/002418 A2 | 1/2010 |
| WO | WO 2010/135495 A2 | 11/2010 |
| WO | WO 2010/138522 A2 | 12/2010 |

OTHER PUBLICATIONS

Desai et al. "Gastrointestinal Uptake of Biodegradable Microparticles: Effect of Particle Size" Pharmaceutical Research (1996), vol. 13, Issue 12, pp. 1838-1845.*
Abdelwahed et al., "Freeze-drying of nanoparticles: Formulation, process and storage considerations" Advanced Drug Delivery Reviews, (2006), vol. 58, pp. 1688-1713.*
International Preliminary Report on Patentability for PCT International Application No. PCT/US2011/022821 dated Jul. 31, 2012.
Annear, D.I., "The preservation of leptospires by drying from the liquid state," J. Gen. Microbiol. (1962), 27, 341-343.
Capela, P., "Effect of cryoprotectants, prebiotics and microencapsulation on survival of probiotic organisms in yoghurt and freeze-dried yoghurt," Food Research International (2006), 39, 203-211.
Crowe, J.H., "The role of vitrification in anhydrobiosis," Annu. Rev. Physiol. (1998), 60, 73-103.
Morgan, C.A., "Preservation of micro-organisms by drying; a review," Journal of Microbiological Methods, (2006), 66, 183-193.
Wong, T.W., "Chitosan and its use in design of insulin delivery system," Recent Patents on Drug Delivery & Formation (2009), 3, pp. 1720-1723.
Tobar et al., Oral Vaccination of Atlantic Salmon Salmo salar against Salmonid rickettsial septicaemia (SRS), abstract, World Aquaculture Society's 2008 annual international conference (May 19-23, 2008).
Tobar et al., Oral Vaccination of Atlantic Salmon Salmo salar against Salmon Rickettsial Septicaemia, presentation, World Aquaculture Society's 2008 annual international conference (May 19-23, 2008).
Supplementary European Search Report dated Sep. 18, 2013 for European Appl. No. 11737688.9.
First Office Action with a Search Report issued by the State Intellectual Property Office of the People's Republic of China on May 22, 2013 for Chinese Application No. 201180007562.3.
Chen et al., Chinese Tropical Medicine, vol. 7, No. 4, pp. 654-655 (2007) (with partial English translation).
Second Office Action issued by the State Intellectual Property Office of the People's Republic of China Feb. 8, 2014 in corresponding Chinese Application No. 201180007562.3, including a Search Report (with English translation).

* cited by examiner

*Primary Examiner* — Abigail Fisher
*Assistant Examiner* — Daniel L Branson
(74) *Attorney, Agent, or Firm* — RatnerPrestia

(57) ABSTRACT

The present invention relates to formulations and methods for stabilizing and protecting of biologic materials during harsh storing and use conditions, wherein the formulations relate to embedded bioactive materials and biologics, including live bacteria, in a protective glassy matrix.

20 Claims, 9 Drawing Sheets

| Process loss of *L. rhamnosus* during drying of different culture type and at different freezing temperatures ||
|---|---|
| Culture Type | Log loss |
| Frozen culture | 0.91 |
| dry Culture | 0.44 |
| Freezing Temperature | |
| +4°C | 0.73 |
| -80°C | 0.96 |
| -180°C | 0.90 |

*the losses for freezing temperatures were evaluated on frozen bacterial cultures*
**Process losses were obtained after drying with no additional purging step.*

Figure 7

DRY GLASSY COMPOSITION COMPRISING A BIOACTIVE MATERIAL

CROSS-REFERENCE TO RELATED APPLICATIONS

This application is filed under the provisions of 35 U.S.C. §371 and claims the priority of International Patent Application No. PCT/US2011/022821 filed on Jan. 28, 2011 which in turn claims priority to U.S. Provisional Application No. 61/299,315 filed in the United States Patent and Trademark Office on Jan. 28, 2010, the content of which is hereby incorporated by reference herein for all purposes.

BACKGROUND OF THE INVENTION

1. Field of the Invention

The present invention relates to stabilizing and protecting of biologic materials during harsh storing and use conditions, and more particularly, the invention relates to embedding bioactive materials and biologics including live bacteria in a protective formulation of an amorphous glassy matrix.

2. Related Art

Freeze-drying has traditionally been the most common method of preserving sensitive biological substances such as live or dead bacteria and viruses and proteins, whereas other methods such as spray drying, fluidized spray drying and desiccation are generally not suitable. The high drying temperatures used in these methods result in significant damage to the bioactive material itself. In addition, they may not sufficiently dry the material to the specific residual moisture or water activity requirements for product stability, and thus an additional drying step by other means, may be required. A conventional freeze drying process typically involves freezing the solution containing the bioactive material, and lyophilizing the frozen biomaterial under full vacuum while it remains frozen. The low temperatures of the freeze-drying process decrease the degradation reaction of the bioactive material and minimize the loss of activity in the final dry form. Often the freeze drying process results in a significant loss of activity and damage to the bioactive material due to the formation of ice crystals during the slow drying process. Furthermore, the freezing step itself, if not done correctly, can denatured or inactivate the bioactive material. Damage caused by the formation of an ice crystals structure may be circumvented, to a certain degree, by the addition of cryoprotective agents to the bioactive solution (Morgan et al., 2006). Such protective agents are highly soluble chemicals that are added to a formulation to protect cell membranes and proteins during freezing and to enhance stability during storage. Common stabilizers for live bacteria and viruses include high sugars such as sucrose, glycerol, or sorbitol, at high concentrations with the cellular material or bioactive (Morgan et al., 2006; Capela et al., 2006). However, such protective agents may not penetrate adequately into the cell to protect active components within the intracellular volume which may lead to instability upon storage of the freeze-dried substances. For this reason, membranous biomaterials such as viruses, bacteria, and cells do not survive well in freeze-drying process. Therefore, a significant challenge remains to develop an optimal drying process and formulation that minimizes drying losses while achieving adequate storage stability of the dried material.

Some of the issues associated with the freeze-drying have been resolved by using a combination of certain formulations and vacuum drying in a glassy state, particularly sugar glasses (U.S. Pat. No. 6,190,701). The dry stabilized bioactive materials are protected in a glassy matrix against hostile environments such as high temperatures and humidity. Generally, stabilization by glass formation is initiated by concentrating the sugar solution containing a bioactive molecule to form supersaturated syrup. Further water removal progressively solidifies the syrup, which eventually turns into a solid sugar glass at low residual water content. Chemical diffusion is negligible in glass and therefore chemical reactions virtually cease. Since denaturation or membrane damages are chemical changes, they cannot occur in the glass and the bioactive material is stabilized and protected. Many glasses fail to stabilize because they react with the bioactive material during storage. Obvious problems occur with reducing sugars, which may form good physical glasses but then their aldehyde groups attack amino groups on the bioactive in a typical Maillard reaction, whereas non-reactive sugars give stable products, which require no refrigeration at all.

Since sugars are inherently hygroscopic, water removal and final drying of the supersaturated syrup become extremely difficult. This drawback was first addressed by (Annear 1962) who developed a formulation containing bacteria in a solution of sugars and amino acids and a vacuum drying process that involves boiling and foam formation of the concentrated syrup. Roser et al. (U.S. Pat. No. 6,964,771) disclosed a similar concept of drying by foam formation that includes a concentration step by evaporating the bulk of the solvent followed by boiling and foaming the concentrated syrup under vacuum. To mitigate the oxidation and denaturation damage that can occur during the boiling step, Bronshtein (U.S. Pat. Nos. 5,766,520, 7,153,472) introduced an improved protective formula containing carbohydrates and surfactants. The drying of the protective solution also involved a stepwise process of concentration under a moderate vacuum before application of a strong vacuum to cause frothy boiling of the remaining water to form dry stable foam. To circumvent the boiling step, Busson and Schroeder (U.S. Pat. No. 6,534,087) have introduced a liquid state drying process of a formulation suitable for sensitive bioactive materials and using a vacuum oven under very mild vacuum pressure above 30 Torr. After achieving a certain level of drying without boiling the material, heat was applied at above 20° C. and dried material was harvested after only a few hours.

This type of drying process, in which the bioactive solution is maintained in a liquid state during the entire drying process, has the advantage of faster drying due to evaporation of the liquid during boiling and the increased surface area presented by the foaming surfaces. However, boiling and foaming require input of a significant amount of heat to provide the necessary eruption of the solution. Such a drying process is not well adapted to drying of sensitive biologicals, such as viable viruses, cells or bacteria because, the applied heat accelerates enzymatic degradation (e.g., proteolysis), and chemical oxidation (e.g., oxidation and free radical attacks), which can destroy the activity or viability of the biological material.

The drying process described above is also limited in its ability to be scaled to a large industrial process. The avoidance of freezing requires the process to be conducted at lower vacuum level (>7 TORR) than in conventional freeze drying or spray freeze drying process cycles. The most significant disadvantage of the above processes is the inability to control and limit the expansion of the foam within the vessel, tray or vial. The uncontrollable eruption and often-excessive foam formation makes it practically impossible to develop an industrial scale process. The eruption and foaming nature of the boiling step results in a portion of material being splattered on the walls of the vessel and into the drying chamber.

To soften the eruption during boiling, Bronshtein (U.S. Pat. Nos. 6,884,866, 6,306,345) has proposed special chambers and a controlled temperature/pressure application protocol that reduces overheating to an acceptable level. Another approach to contain the eruption and excessive foaming is described in US. Pat. Publication No. 2008/0229609, in which the bioactive solution is enclosed in a container or a bag covered with breathable membranes. Once again, these protocols are difficult to implement in industrial level, they require special equipment and are difficult to reliably reproduce with different formulations.

The dry foam process, as it known in the art, is not particularly well adapted to preservation of membranous biological materials, such as liposomes, viruses or viable cells and bacteria. Lipid membranes often prevent penetration of the protective agents into enclosed volumes or prevent adequate removal of water from the enclosed volume. Without adequate penetration of protective agents, enzymatic processes, such as proteolysis, and chemical processes, such as oxidation and free radical attacks, can destroy the activity or viability of the membranous biological material. Hypoosmotic fluids remaining within membrane enclosed volumes can promote instability of the biological material. Truong-le, Vu (U.S. Pat. No. 7,381,425) describes a freeze drying process suitable for membranous bioactives. Compositions of the invention include a polyol and a membranous bioactive material. The drying process starts by cooling the formulation to a temperature of about a phase transition temperature of the lipid membranes, reducing pressure on the formulation to form stable foam, freezing the foam, and then sublimating water from the frozen foam to provide a lyophilized dry foam composition. Secondary drying conditions can be employed to further dry the foam.

A need remains for a suitable protective formulation that can be dried in glassy state without boiling and excessive foaming. There is a need particularly for a cost effective formulation and scalable drying process that is also suitable for applications outside the pharmaceutical industry such as food and agriculture industries. Protective formulations and mild drying processes are required to provide adequate drying without exposure to high temperatures. A composition is needed that can protect such biologicals in storage under high temperature and humid conditions. The present invention provides a solution to all of these challenges as is described below. The dehydration process of the present invention is very gentle and does not expose the active agent to boiling or foaming and is therefore advantageous over conventional freeze drying and foam drying techniques which would subject the sample to one or both of these stresses.

SUMMARY OF THE INVENTION

The present invention includes compositions and drying methods for preserving sensitive bioactive materials, such as peptides, proteins, enzymes, hormones, vitamins, carotenoids, minerals, drugs, antibiotics, microbiocides, fungicides, herbicides, insecticides, spermicides, nucleic acids, antibodies, vaccines, bacteria (probiotic or otherwise), viruses and/or cell suspensions in storage. The drying methods provide a process for drying of a formulation comprising the bioactive materials, a matrix forming agent, and a glass forming agent. The formulation is prepared by dispersing all the solid components and the bioactive materials in a solution. The solution is snap-frozen by means known in the art such as liquid nitrogen or dry ice to form an amorphous composition in small beads, strings or droplets. The frozen particles can be stored in a deep-freezer (between −30° C. and −80° C.) until drying or immediately placed on trays in a frozen amorphous state for liquid drying in a conventional freeze dryer. The drying method is initiated by a short purging and structure stabilizing step of the frozen particles under a vacuum pressure of less than <2000 mTORR followed by a primary drying step under higher than >2000 mTORR of vacuum pressure and at a desired temperature. During the secondary and final drying step of the glassy amorphous material, a full vacuum pressure and elevated temperature are applied, to achieve a final desirable water activity of the dry material.

In one embodiment, the formulation comprises sufficient amounts of matrix forming agents, in which the bioactive material is embedded. Examples of a suitable matrix agent include, but are not limited to, cellulose acetate phthalate (CAP), carboxy-methyl-cellulose, pectin, sodium alginate, salts of alginic acid, hydroxylpropyl methyl cellulose (HPMC), methyl cellulose, carrageenan, guar gum, gum acacia, xanthan gum, locust bean gum, chitosan and chitosan derivatives, collagen, polyglycolic acid, starches and modified starches, cyclodextrins and oligosaccharides (inulin, maltodextrins, dextrans, etc.); and combinations thereof. In one particular embodiment, the preferred matrix forming agent is sodium alginate. Preferably, the formulation comprises, in percent by weight of total dry matter, 0.1-20% and more preferably 1-12%.

In an additional embodiment, the matrix forming agent comprises a mixture of sodium alginate and oligosaccharides in a weight ratio of 1:1-10, more preferably 1:1-5 of sodium alginate/oligosaccharides.

In yet another embodiment of the present invention, the matrix forming agent is cross-linked with divalent metals ions to form a firm hydrogel. The cross-linked hydrogel formulation is formed by atomizing or extruding the slurry in a bath containing divalent metal ions solution or by adding divalent metal ions directly into the slurry and allowing the formulation to harden and form a hydrogel. The hydrogel formulation is then flash frozen and dried according to the drying methods of the invention.

In yet another embodiment, the formulation comprises significant amounts of glass forming agents, in which the microorganisms are embedded. Examples of a suitable agent include but are not limited to proteins such as egg albumen, egg white, gelatin, immunoglobulin, isolated soy protein, wheat protein, pea protein, cotton seed protein skim milk powder, caseinate, whey protein and any hydrolyzed protein; carbohydrates including monosaccharides (e.g., galactose, D-mannose, sorbose, etc.), disaccharides (e.g., lactose, trehalose, sucrose, etc.), an amino acid such as lysine, glutamate, glycine, alanine, arginine or histidine, as well as hydrophobic amino acids (tryptophan, tyrosine, leucine, phenylalanine, etc.); a methylamine such as betaine; an excipient salt such as magnesium sulfate; a polyol such as trihydric or higher sugar alcohols, (e.g. glycerin, erythritol, glycerol, arabitol, xylitol, sorbitol, and mannitol); propylene glycol; polyethylene glycol; pluronics; surfactants; and combinations thereof.

In one preferred embodiment, the glass forming agent comprises a mixture of a disaccharide and a hydrolyzed protein. In a particular embodiment, the preferred glass forming agent is a mixture of trehalose and hydrolyzed protein. Preferably, the formulation comprises, in percent by weight of total dry matter, 10-90%, of trehalose and 0.1-30% hydrolyzed protein, more preferably 20-80% of trehalose and 0.1-20% hydrolyzed protein, and most preferably 40-80% of trehalose and 0.1-20% hydrolyzed protein.

The method of the invention typically includes mixing in a solution bioactive materials (e.g., peptides, proteins, enzymes, hormones, vitamins, carotenoids, minerals, drugs, antibiotics, microbiocides, fungicides, herbicides, insecticides, spermicides, nucleic acids, antibodies, vaccines, bacteria, viruses and/or cell suspensions), at least one matrix forming agent, and at least two glass forming agents into a homogeneous slurry, snap-freezing the slurry by atomizing, dropping or extruding into liquid nitrogen bath. Collecting the beads, microbeads, strings or droplets from the liquid nitrogen bath and drying in a liquid state in a freeze drier, or alternatively storing them in a deep freezer (between −30° C. and −80° C.) until drying.

In a variation of the present invention, the amount of the matrix forming agent in the formulation is adjusted to achieve a desired formulation viscosity and density that allowed an efficient primary drying while avoiding boiling and excessive foaming that typically occur during the primary liquid drying step. A desired density of the liquid formulation can be achieved by any means known in the art, for example, whipping or injecting gas such as air, nitrogen, carbon dioxide, argon etc. Preferably, nitrogen is injected into the viscous slurry formulation under mixing to form stable porous or creamy slurry before the snap-freezing step.

According to the invention, the drying process involves three major steps; 1. Short purging and structure stabilizing step of the frozen particles under a vacuum pressure of less than <2000 mTORR, 2. Primary liquid drying step under vacuum pressure of more than >2000 mTORR and at a desired temperature, 3. Secondary and final drying step of the glassy material under full vacuum pressure and elevated temperature for a time sufficient to reduce the water activity of the dried formulation to 0.3 Aw or less.

In preferred embodiments of the drying methods, the bioactive material is mixed in a solution including a matrix forming agent and a glass forming agent. In one particular embodiment, the bioactive material comprises live bacteria (e.g., probiotic bacteria). Examples of suitable microorganisms include, but are not limited to, yeasts such as *Saccharomyces, Debaromyces, Candida, Pichia* and *Torulopsis*, molds such as *Aspergillus, Rhizopus, Mucor, Penicillium* and *Torulopsis* and bacteria such as the genera *Bifidobacterium, Clostridium, Fusobacterium, Melissococcus, Propionibacterium, Streptococcus, Enterococcus, Lactococcus, Kocuriaw, Staphylococcus, Peptostrepococcus, Bacillus, Pediococcus, Micrococcus, Leuconostoc, Weissella, Aerococcus, Oenococcus* and *Lactobacillus*. Specific examples of suitable probiotic microorganisms would be represented by the following species and include all culture biotypes within those species: *Aspergillus niger, A. oryzae, Bacillus coagulans, B. lentus, B. licheniformis, B. mesentericus, B. pumilus, B. subtilis, B. natto, Bacteroides amylophilus, Bac. capillosus, Bac. ruminocola, Bac. suis, Bifidobacterium adolescentis, B. animalis, B. breve, B. bifidum, B. infantis, B. lactis, B. longum, B. pseudolongum, B. thermophilum, Candida pintolepesii, Clostridium butyricum, Enterococcus cremoris, E. diacetylactis, E faecium, E. intermedius, E. lactis, E. muntdi, E. thermophilus, Escherichia coli, Kluyveromyces fragilis, Lactobacillus acidophilus, L. alimentarius, L. amylovorus, L. crispatus, L. brevis, L. case* 4 *L. curvatus, L. cellobiosus, L. delbrueckii ss. bulgaricus, L farciminis, L. fermentum, L. gasseri, L. helveticus, L. lactis, L. plantarum, L. johnsonii, L. reuteri, L. rhamnosus, L. sakei, L. salivarius, Leuconostoc mesenteroides, P. cereviseae (damnosus), Pediococcus acidilactici, P. pentosaceus, Propionibacterium freudenreichii, Prop. shermanii, Saccharomyces cereviseae, Staphylococcus carnosus, Staph. xylosus, Streptococcus infantarius, Strep. salivarius ss. thermophilus, Strep. Thermophilus* and *Strep. lactis*.

In preferred methods, the formulation is mixed at room temperature or slightly warmed to assist in solubilizing the materials into viscous solution (e.g., from 20° C. to 40° C.). After mixing to homogeneity, the viscous slurry is then snap-frozen by atomizing, dripping, or extruding into liquid nitrogen. The frozen particles are harvested from the liquid nitrogen bath and are immediately dried or alternatively stored in a deep freeze for later drying. Typically, the slurry containing the bioactive is snap-frozen to between −30° C. to −180° C., more preferably the formulation is snap-frozen in liquid nitrogen.

In a preferred embodiment, the snap-frozen particles are immediately dried or otherwise stored in a deep freezer, preferably at −80° C., until drying. The frozen particles are then loaded on trays and immediately transferred to a vacuum drying chamber where they are dried according to the present invention. Preferably, the drying is initiated by subjecting the frozen particles under vacuum pressure between 0 and 2000 mTORR. The frozen particles are degassed and their structure and volume allowed to develop and stabilize for a short period of time. Typically, the desirable time period for subjecting the frozen particle to high vacuum pressure is no more than 30 minutes, more preferably the time period is between 1 and 20 min. After the short initial degassing and structure stabilizing of the frozen particles the vacuum is adjusted to between 2000 and 10,000 mTORR and heat applied to thaw the particles at a temperature above their freezing point. Typically, the vacuum is adjusted to between 2000 and 4000 mTORR and the particle temperature is increased to between −5° C. and +5° C. Under these preferred primary drying conditions the frozen particles are rapidly thawed and loosely maintain their original shape while an accelerated dehydration begins. The subsequent secondary drying is established after removing about 60-90% of the free water, a maximum vacuum pressure is applied and heat supplying temperature to the formulation is elevated to from 30° C. to 60° C. To maximize the stability of the final product, the formulation is preferably dried for a time sufficient to reduce the water activity of the formulation to Aw=0.3 or less. In a preferred embodiment of the invention, the secondary drying comprises removal of bound water at a pressure of less than 1000 mTORR.

The dried formulation can be used directly as a flake, or ground into a powder and sieved to an average particle size from about 10 μm to about 1000 μm. The formulation can be administrated directly to an animal, including man, as a concentrated powder, as a reconstituted liquid, (e.g., beverage), or it can be incorporated either in flake or powder form into an existing food or feed product.

BRIEF DESCRIPTION OF THE FIGURES

FIG. 7. Process and drying losses of *L. rhamnosus* in compositions and drying methods of the invention.

DETAILED DESCRIPTION OF THE INVENTION

Definitions

Figure 1:
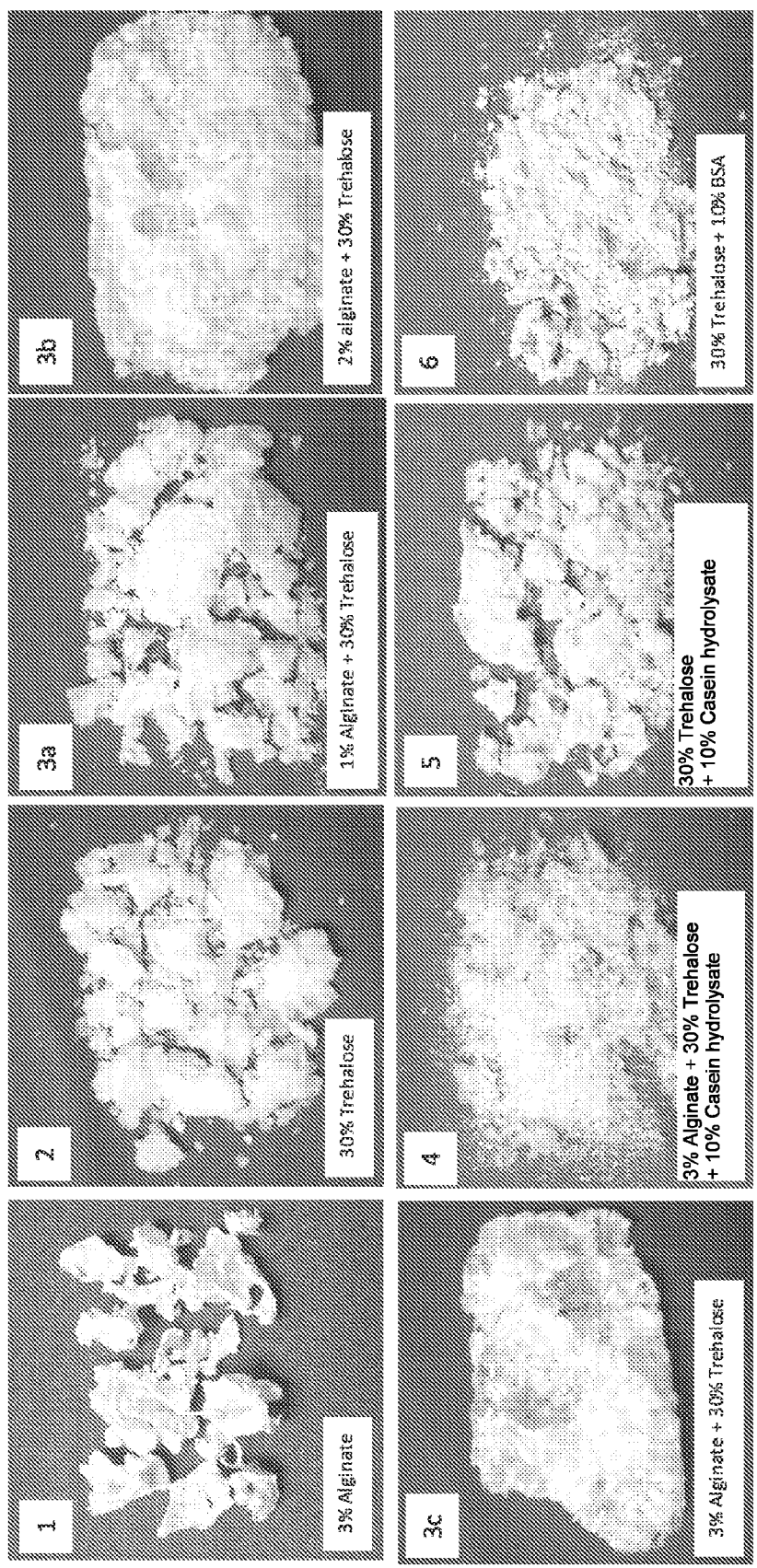
FIG. 1. Visual and microscopic observations of different dried compositions containing various matrices and glass forming agents as frozen solid bead according to the method of the present invention.
Figure 1:
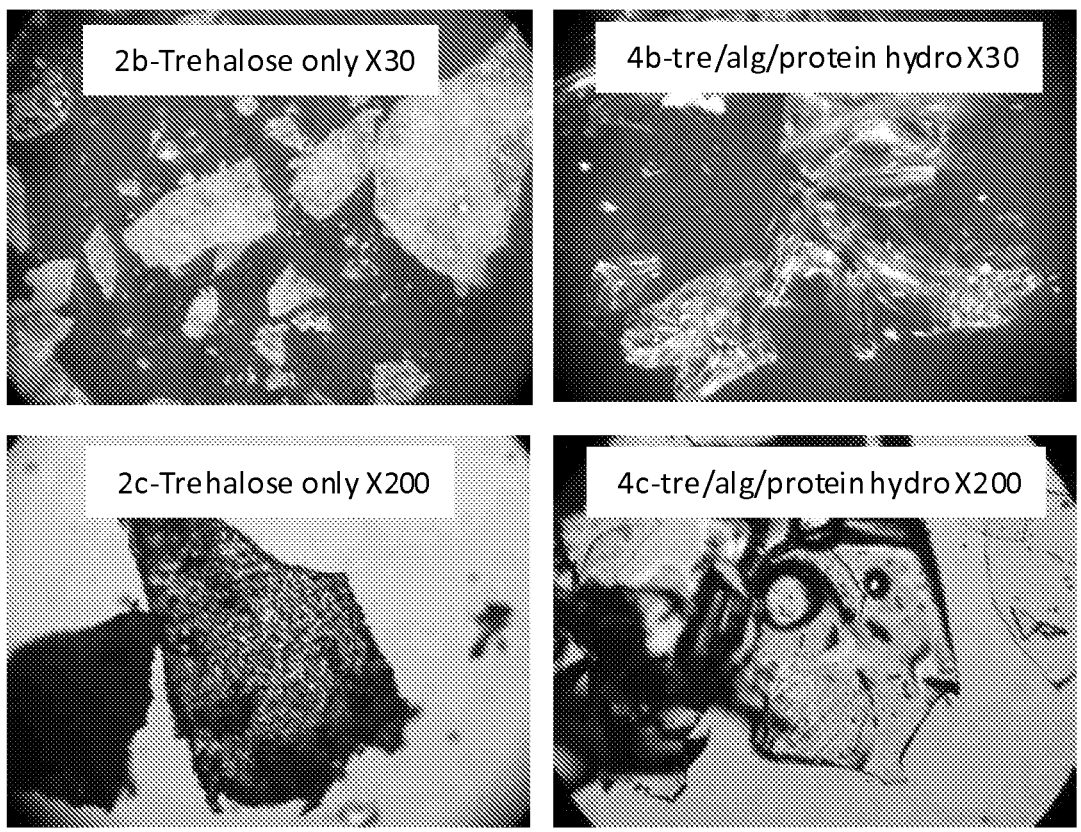
Figure 2:
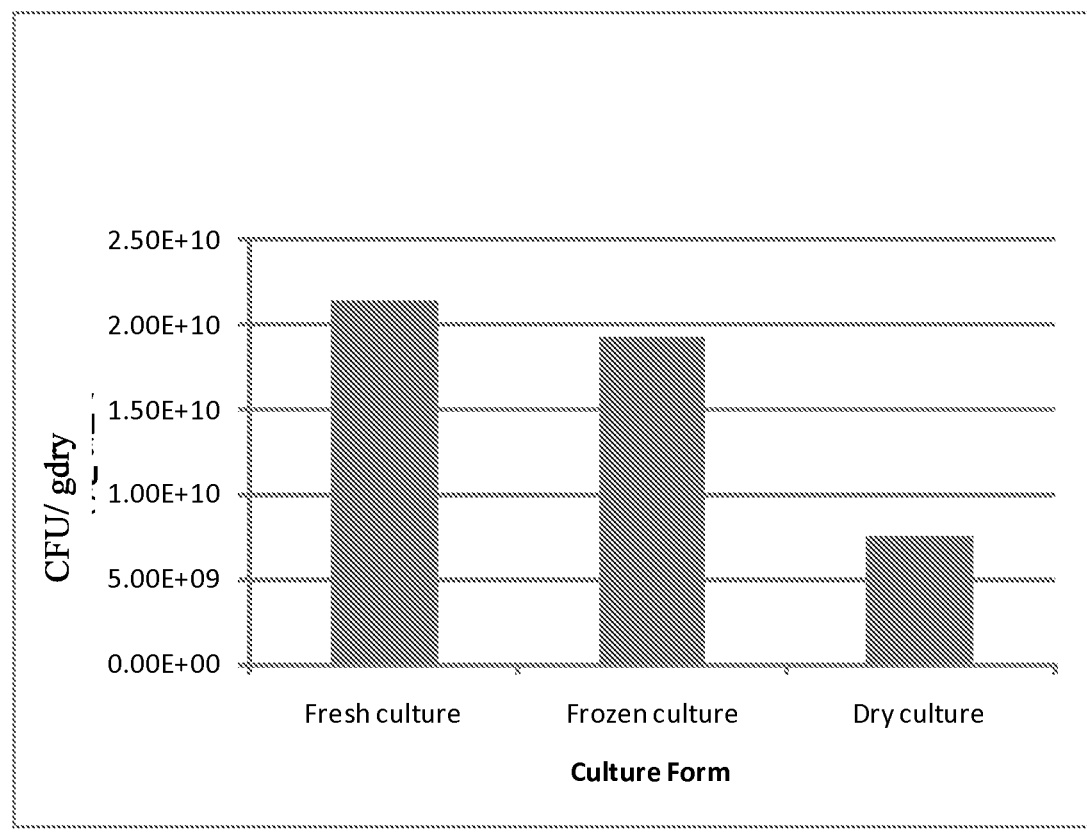
FIG. 2. The effect of *L. rhamnosus* culture form as fresh, frozen beads or dry powder cultures on its initial CFU counts in a dry composition.

It is to be understood that the terminology used herein is for the purpose of describing particular embodiments only, and is not intended to be limiting.

As used in this specification and the appended claims, the singular forms "a," "an" and "the" include plural referents unless the content clearly dictates otherwise. Thus, for example, reference to "a protein" includes singular protein or a combination of two or more proteins; reference to "enzyme", "vitamin", "bacteria", etc., includes singular or mixtures of several, and the like.

"Bioactive material," "bioactive composition," or "bioactive formulation" refers to preparations, which are in such a form as to permit the biological activity of the bioactive ingredients to be unequivocally effective.

"Matrix forming agent" refers to compounds or materials that are added to the formulation to increase the viscosity and or the density of the wet formulation or to form a hydrogel. Examples of a suitable matrix forming agent include but are not limited to water soluble cellulose derivatives such as methylcellulose, hydroxypropylcellulose, hydroxyethylcellulose, and hypromellose; alginates, galactomannan, gellan gum, tragacanth, including any derivatives of these, cellulose acetate phthalate (CAP), carboxy-methyl-cellulose, pectin, sodium alginate, salts of alginic acid, hydroxylpropyl methyl cellulose (HPMC), methyl cellulose, carrageenan, guar gum, gum acacia, xanthan gum, locust bean gum, chitosan and chitosan derivatives, collagen, polyglycolic acid, starches and modified starches, cyclodextrins and oligosaccharides (inulin, maltodextrins, dextrans, etc.) and combinations thereof.

"Glass forming agent" or "sugar glass forming agent" generally refers to compounds or materials that are readily soluble in a solution and do not thicken or polymerize upon contact with water. These agents are added to ensure or increase the stability of the bioactive material during the drying process and afterwards, or for long-term storage stability of the dry powder product. Useful glass forming agents can be monomeric, oligomeric or polymeric.

According to one of the preferred embodiments, the glass forming agents is a saccharide. A saccharide, or carbohydrate, is defined as a compound predominantly composed of carbon, hydrogen, and oxygen. Useful saccharides include reducing and non reducing sugars and sugar alcohols, oligosaccharides, water soluble polysaccharides and derivatives thereof. Preferred saccharides according to the invention include glucose, fructose, lactose, sucrose, trehalose, maltose, cellobiose, galactose, maltotriose, raffinose, dextrin, dextran, inulin, mannitol, sorbitol, xylitol. Particularly preferred saccharides are glucose and trehalose.

Other useful glass forming agents may be selected from other chemical classes, such as water soluble amino acids, peptides or proteins and hydrolyzed protein. For example, lysine, glycine, alanine, arginine or histidine, as well as hydrophobic amino acids (tryptophan, tyrosine, leucine, phenylalanine, etc.); a methylamine such as betaine. Useful proteins include gelatine, egg albumin, egg white, whey protein, caseinate, immunoglobulins, soy protein, pea protein, cottonseed protein or other food, dairy or vegetable proteins.

"Hydrolyzed proteins" generally refers to proteins either from animal, dairy or plant source that were broken down by enzymatic hydrolysis or digestion into shorter peptide fragments and/or amino acids. Useful hydrolyzed proteins are those subjected to an extensive hydrolysis process that reduces the molecular weight of 99% of the native proteins to bellow 50,000 Dalton, preferable to bellow 10,000 Dalton.

"Ambient" room temperatures or conditions are those at any given time in a given environment. Typically, ambient room temperature is 22-25° C., ambient atmospheric pressure, and ambient humidity are readily measured and will vary depending on the time of year, weather and climactic conditions, altitude, etc.

"Purge" or "Degassing" in the context of the present invention refers to the release of a gas from a solid or liquid formulation wherein the partial pressure of the gas is greater than the applied pressure. This is not boiling of solution in liquid form, and can often occur at pressures above a pressure that would boil a solution.

"Boiling" refers to the rapid phase transition from liquid to gas that takes place when the temperature of a liquid is above its boiling temperature. The boiling temperature is the temperature at which the vapor pressure of a liquid is equal to the applied pressure. Boiling can be particularly vigorous when heat is added to a liquid that is already at its boiling point.

"Water activity" or "Aw" in the context of dried formulation compositions, refers to the availability of water and represents the energy status of the water in a system. It is defined as the vapor pressure of water above a sample divided by that of pure water at the same temperature. Pure distilled water has a water activity of exactly one or Aw=1.0.

"Relative Humidity" or "RH" in the context of storage stability refers to the amount of water vapor in the air at a given temperature. Relative humidity is usually less than that required to saturate the air and expressed in percent of saturation humidity.

"Dry" and variations thereof refer to a physical state that is lyophilized, dehydrated or anhydrous, i.e., substantially lacking liquid. Drying includes for example, spray drying, fluidized bed drying, lyophilization, and vacuum drying.

"Lyophilize" or "Freeze drying" refers to the preparation of a composition in dry form by rapid freezing and dehydration in the frozen state (sometimes referred to as sublimation). This process may take place under vacuum at a pressure sufficient to maintain frozen product, preferably lower than about <2000 mTORR.

"Primary drying" or "Liquid drying", with regard to processes described herein, refers to the dehydration drying that takes place from the time of thawing the frozen particles to the point where secondary drying starts. Typically, the bulk of primary drying takes place by extensive evaporation, while the product temperature remained significantly lower than the temperatures of the heat source. This process may take place under vacuum at a pressure sufficient to maintain thawed product, preferably greater than about >2000 mTORR.

"Secondary drying", with regard to processes described herein, refers to a drying step that takes place at temperatures above freezing temperatures of the formulation and near the temperature of the heat source. This process may take place under vacuum at a pressure sufficient to reduce the water activity of a formulation, preferably less than about <1000 mTORR. In a typical formulation drying process, a secondary drying step reduces the water activity of the formulation to an Aw of 0.3 or less.

"Foam formation" refers to a procedure for drying sensitive biologics by boiling under vacuum under conditions wherein the biologics retain activity or viability for extended periods of time at ambient and higher temperatures. The specific procedure for the formation of a mechanically stable porous structure proceed in two steps; (1) Primary Foam-Drying and by boiling under a vacuum (2) Stability Drying/Vitrification, and are disclosed in U.S. Pat. No. 5,766,520 to Bronshtein.

A "stable" formulation or composition is one in which the biologically active material therein essentially retains its physical stability, chemical stability, and/or biological activity upon storage. Stability can be measured at a selected temperature and humidity conditions for a selected time period. Trend analysis can be used to estimate an expected shelf life before a material has actually been in storage for that time period. For live bacteria, for example, stability is defined as the time it takes to lose 1 log of CFU/g dry formulation under predefined conditions of temperature, humidity and time period.

"Viability" with regard to bacteria, refers to the ability to form a colony (CFU or Colony Forming Unit) on a nutrient media appropriate for the growth of the bacteria. Viability, with regard to viruses, refers to the ability to infect and reproduce in a suitable host cell, resulting in the formation of a plaque on a lawn of host cells.

The compositions and methods of the present invention solves the problem of providing a cost effective and industrially scalable drying processes for formulations containing sensitive bioactive materials, such as peptides, proteins, enzymes, hormones, vitamins, carotenoids, minerals, drugs, antibiotics, microbiocides, fungicides, herbicides, insecticides, spermicides, nucleic acids, antibodies, vaccines, bacteria, viruses and/or cell suspensions, with a significantly extended lifetime in the dry state.

The invention provides a composition comprising a bioactive material and matrix and glass forming agents in a solution mixture and a drying method comprising snap-freezing said composition in liquid nitrogen to form an amorphous solid structure in a form of droplets, strings, beads or microbeads and purging the frozen particles under high vacuum followed by stabilizing the bioactive material in a sugar glass formation by lyophilizing or evaporating the moisture under a regimen of reduced pressure while supplying heat to the composition.

Most of the viability loss of microorganism during drying processes can be attributed to a combination of ice crystal formation, high osmotic and oxidative stresses, shear forces and energy release during bubble cavitations associated with the "boiling" and foaming of the solution under low drying pressure and high temperature. The present invention avoids such negative effects and provides compositions and drying methods with a minimal loss and which results in a bioactive material protected in sugar glass matrix under harsh storage and handling conditions thereafter.

Compositions of the Invention

The present invention includes compositions of a bioactive material, a matrix forming agent and glass forming agents in a viscous solution. The formulations of the invention were found to be inherently different in their physical structure and function from non-viscous or concentrated formulations that were dried with or without snap-freezing and purging. For example, formulations of the prior art were initially "foamed" by boiling to facilitate effective drying. The foaming step generally resulted in an extensive boiling and eruption of the solution that is an unavoidable consequence of the drying in a liquid state and as a result, only a very low loading capacity of material in a vial or a vessel can be achieved (see for example U.S. Pat. No. 6,534,087, in which the thickness of the final foamed product is less than 2 mm).

The compositions and drying methods of the present invention avoid boiling and extensive foaming of the formulation thereby enabling much higher loading of material per drying area and, as a result, can be easily scaled up to the production of large quantities of material without the use of specifically designed vessels, trays or equipment.

Figure 8:
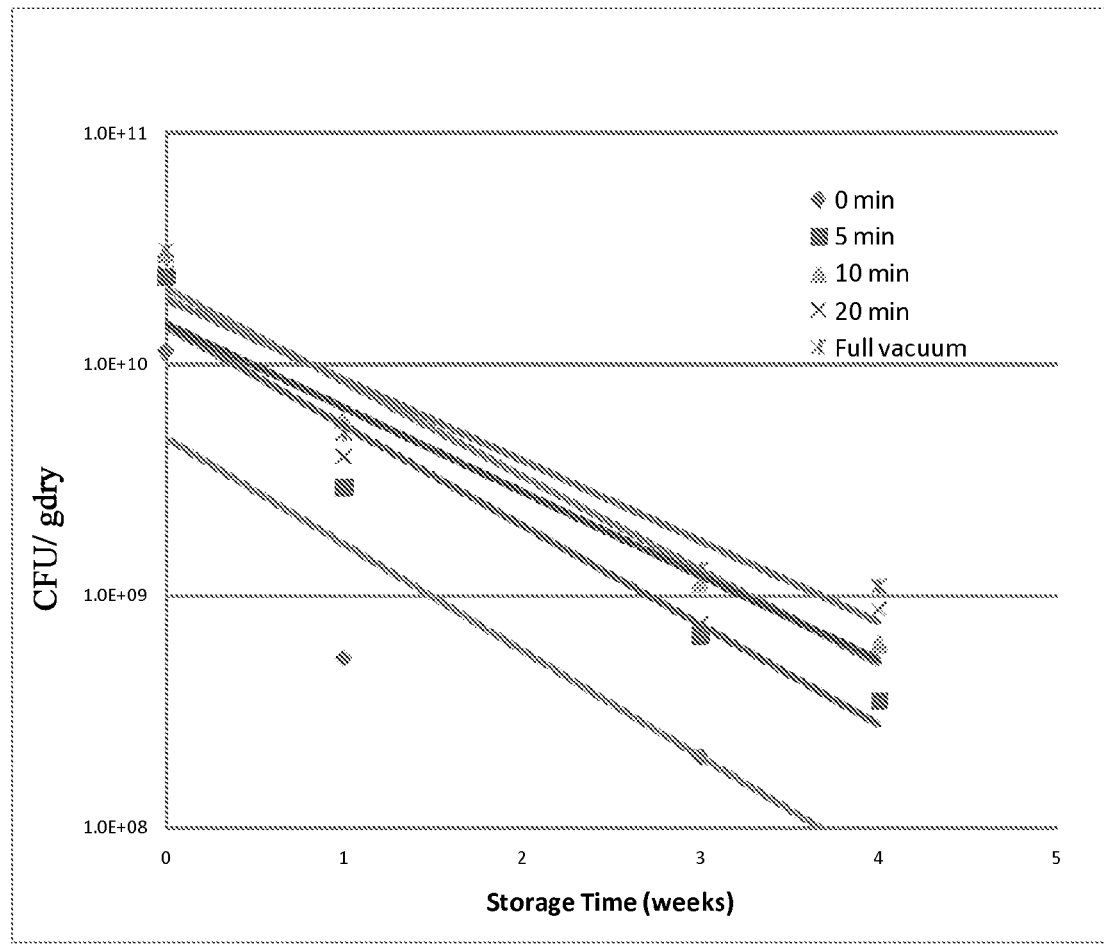
FIG. 8. Stability trends of dry probiotic bacteria, *L. rhamnosus* composition in storage at 40° C. and 33% relative humidity.

Probiotic bacteria have been shown to benefit particularly from the formulations and drying methods of the present invention. The formulation is prepared according to the compositions and methods of the invention including mixing fresh, frozen or dry cultures of probiotic bacteria with at least one matrix forming agent and at least two glass forming agents, snap-freezing the viscous formulation in liquid nitrogen to form an amorphous structure of frozen solid droplets, strings or beads. For primary drying, sufficient vacuum pressure is applied to purge and stabilize the structure of the frozen particles and then the frozen particles are lyophilized or evaporated under reduced vacuum pressure and increased temperature above the freezing temperature of the formulation. Maintaining the temperature of the formulation above the freezing point can be accomplished by conduction of heat away from the formulation, and/or by loss of latent heat due to water evaporation. To complete the drying process and further reduce the water activity of the formulation, a secondary drying step can be applied, at higher vacuum pressure of 1000 mTORR and lower and at elevated temperature up to 70° C., to provide a final composition with water activity with an Aw of 0.3 or lower. Such a composition can remain stable in storage conditions of 40° C. and 33% RH for 30 days or more, as shown in FIG. 8.

Preparation of the Compositions

The materials, to be mixed in a solution with the preferred bioactive for the preparation of dry powder compositions according to the invention, include at least one matrix forming agent and at least two glass forming agents. Such materials, when mixed with the preferred bioactive material form beads, microbeads, strings or droplets in liquid nitrogen and can be efficiently lyophilized or dehydrated in an amorphous glassy state according to methods of the invention and to provide large quantities of stable dry compositions for storage and administration of said bioactive material (see FIG. 1A & B for visual and microscopic observations and water activity (Aw) of different formulations after drying). The matrix forming agent provides structural stability to the formulation, enhanced drying profile and/or physical and chemical protective benefits to the bioactive materials. The matrix forming agent also provides thickening viscosity to the formulation and better control over the formulation properties under vacuum pressure and increased structural strength to the dried formulation compositions of the invention (see FIG. 1B—Pictures 4, 4*b*, 4*c* for the glassy structure and dryness of that particular formulation). The matrix forming agent includes a mixture of polysaccharides and oligosaccharides. The preferred polysaccharides, particularly for live organisms, are water soluble gums, because of their distinctive characteristic to form viscous gel at mild temperatures. Gums at certain concentration were also found to effectively stabilize the formulation and facilitate the formation of an amorphous glassy structure and enhance drying profile under vacuum (see FIG. 1A—pictures 3*a*, 3*b*, 3*c*, 4, and FIG. 1B-4*c* and FIG. 6).

Notably by viewing the pictures of FIG. 1A in combination with the results set forth below in Table 1, it is evident that samples 3b, 3c, 4, 5, and 6 were all dried sufficiently to provide some porosity in the amorphous glassy structures.

TABLE 1

Visual Inspection of the Various Dry Compositions

|  | 1 | 2 | 3a | 3b | 3c | 4 | 5 | 6 |
|---|---|---|---|---|---|---|---|---|
| Dryness | Not Dry | Not Dry | Not Dry | Dry | Dry | Dry | Dry | Dry |
| Porousness | None | None | None | Present | Present | Present | None | Partial |
| Aw | 0.847 | 0.923 | 0.916 | 0.216 | 0.183 | 0.376 | 0.171 | 0.112 |
| Glass Structure | None | None | None | Partial | Partial | Present | Partial | Partial |

Glass forming agents of the invention can include various sugars, non-reducing sugars, sugar alcohols, amino acids, proteins, hydrolyzed proteins and peptides. The glass forming compound is preferably one that does not crystallize and/or destabilize the biologically active material in the formulation at freezing temperatures (e.g., lower than −20° C.). For example, bioactive material can be physically embedded in amorphous sugar glass structures such as sucrose or trehalose to promote retention of molecular structure throughout the drying process and impart structural rigidity to the amorphous matrix in the dry state. The glass forming agent replaces water of hydration lost during drying, to prevent damage to cell membranes and denaturation of enzymes (see review by Crowe et al., 1998). Other functions of the glass forming agent can include protecting the bioactive material from exposure to damaging light, oxygen, oxidative agents and moisture. Most glass forming agents must be readily dissolved in a solution in amounts ranging from about 0.1 weight percent to about 80 weight percent. It is beneficial to include two or more different glass forming agents to inhibit the formation of crystals and enhance the stability of the dried bioactive material formulation in storage conditions for extended time periods (see the effect of sugars and proteins mixture in FIG. 1A—pictures 4, 5 and 6).

The pre-dried formulations include a substantial amount of total solids (constituents minus the solvent, such as water). A major portion of the total solids consist of the bioactive material, the matrix forming agents and the glass forming agents. For example, the bioactive material is present in the formulation in a concentration ranging from about 5-60 weight percent, the matrix forming agent from about 1-20 weight percent, and the glass forming agent from about 5-80 weight percent. In another example, the matrix forming agent can be present in the formulation in a concentration ranging from about 0.5-10 weight percent, and the glass forming agent from about 10-50 weight percent. Preferably, the wet formulation should have solids content between about 5% and 80%; more preferably between 30% and 60%. The viscosity of formulations of the invention is typically greater than 1000 centipoises (cP); more preferably, greater than 5,000 cP; and most preferably greater than 10,000 cP. The density of the formulations of the invention is preferably between 0.9 and 1.2 g/ml.

Methods of Preparing Stable Dry Formulations

Methods for preparing stable dry formulations containing bioactive materials include; (1) preparation of a formulation by mixing the bioactive material with matrix and glass forming agents in a solution, (2) snap-freezing the formulation to form solid frozen particles, (3) subjecting the frozen particle to high vacuum pressure for a short time to purge the particles and stabilize their structure, (4) removing water by lyophilizing and/or evaporating the moisture under reduced pressure while supplying heat to the formulation at a temperature above the formulation freezing temperature, preferably higher than −10° C., (5) further reducing the formulation water activity to lower than 0.3 Aw under full vacuum and elevated temperature.

In one embodiment, for example, the formulations of the invention includes a bioactive material formulated into a solution or suspension containing a matrix and glass forming agents. The matrix forming agent and/or high concentration of glass forming agents are dissolved and sanitized in hot aqueous solution with agitation before cooling and mixing with the bioactive material. The bioactive material, such as cultured virus or bacterium, is concentrated and separated from the culture media by centrifugation or filtration before re-suspension into the formulation.

In one embodiment of the present invention, the totality of the water in the formulation is provided in the liquid of the concentrated live organism and the live organism suspension is maintained at a temperature slightly above room temperature. The dry components are blended together and then slowly added to the warm (25° C. to 40° C.) suspension of the live organism. The formulation suspension is gently agitated in a planetary mixer until all components are fully dispersed and uniform slurry is obtained.

The viscous solution is then snap-frozen by atomizing, dripping or extruding in liquid nitrogen bath to form small solid droplets strings or beads. The frozen solid particles may be stored in a deep freezer between −30° C. and −80° C. until drying or immediately placed on trays and lyophilized or dried according to the methods of the invention. The solid frozen particles is purged for a short time, typically between 1 and 20 minutes, under sufficient vacuum (e.g., below <2000 mTORR). Generally the particles remain in a solid frozen form at a temperature below −20° C. during the purging step. After the initial purging step the vacuum pressure is increased to between 2000 and 10,000 mTORR and heat may be provided allowing the formulation temperature to rapidly increase to between −5° C. and +5° C. and particles begin to thaw. Once the formulation temperature reached the desired temperature, heat is adjusted to maintain that temperature and the primary drying step is progressed. At this step the formulation is already thawed and accelerated water evaporation take place without any boiling or foaming.

Typical methods in the prior art involve extensive foaming and/or splattering and violent boiling that can be damaging to sensitive biologicals and cause difficulties for industrial scale up at high loading capacity (see for example U.S. Pat. No. 6,534,087, where the applied vacuum pressure result in violent boiling and foaming), whereas the current compositions and methods avoid any boiling or excessive foaming of the formulation while achieving a significantly faster drying rate and enables a high loading capacity of the formulation. Additionally, a complete and efficient degassing of viscous liquid slurries is difficult and may require an extended period of time. These obstacles were all resolved in the present invention by using a suitable composition that allows an effective primary liquid drying that forms an amorphous glassy formation without any boiling and excessive foaming. Surprisingly and importantly this was mainly achieved by snap-freezing of a suitable composition and through the introduction of a short purging step before the start of the primary liquid drying step. The loading of solid frozen particles on a tray as opposed to slurry or viscous syrup allows much higher loading capacity per drying area on trays than was afforded according to the prior art. After the primary liquid drying stage is completed, the stabilized amorphous glassy formulation is held at elevated secondary drying temperatures (between 20° C. and 70° C.) and vacuum pressures of less than 1000 mTORR to further reduce the water activity of the formulation in a very short time.

Another embodiment of the invention provides methods to prepare hydrogel formulation compositions for preservation of bioactive materials. For example, a formulation containing a bioactive material and matrix and glass forming agents are mixed in a solution and cross-linked to form firm hydrogel particles by atomizing or extruding in a bath containing divalent metal ions or by adding divalent metal ions directly into the slurry and shredding the harden hydrogeled slab to small strings or pieces. The hydrogeled particles are then dried according to the drying methods of the invention as described above.

In one particular embodiment of the invention, for example, the formulation includes live probiotic bacteria in a solution of 1-4% sodium alginate and 10-40% trehalose. Proteins and particularly hydrolyzed proteins, such as casein, whey, pea, soy or cottonseed is added to the formulation at 5-10% to enhance the drying process and the formation of an amorphous glassy stable structure of the formulation (see FIG. 1A, pictures 4, 5 and 6). The probiotic culture can be fresh, frozen or already dried in a form of dry powder (see FIG. 2 for the CFU counts of different culture forms of probiotic bacteria in dry formulation) The solution is mixed at a temperature slightly above the room temperature (typically between 25° C.-37° C.) until all the components are completely dissolved. The formulation slurry is atomized, extruded or dripped in liquid nitrogen to form small droplets or beads which are then removed from the liquid nitrogen, packed in bags and can be stored in a deep freezer at –80° C. until drying.

A typical drying method of live probiotic bacteria include; spreading the solid frozen beads on trays in a uniform layer at a loading capacity between 100-1000 g/sq ft and the trays are immediately placed in a freeze drier. Vacuum pressure is then applied at about 1000 mTORR and depending on the freeze drier size and type of heat source, the shelf temperature adjusted to +20° C. or to a temperature sufficient to maintain the particles at about –20° C. The solid frozen beads are allowed to purge for about 5-30 minutes and vacuum adjusted to between 2000 and 10,000 mTORR and heat transfer increased to raise the formulation temperature to between –5° C. and +5° C. These temperature and vacuum pressure conditions are maintained during the primary liquid drying step which may last from a few hours and up to 24 hours depending on the tray loading, preferably from about 3 to 10 hours. At some point during the primary drying process, the rate of evaporation of solvent slows and the formulation temperature begins to increase due to superfluous supply of heat in the drying chamber. This point indicates the end of the primary drying step. As solvent is driven out from the formulation, the glass forming agents in the solution become concentrated and thicker until it stops flowing as a liquid and form an amorphous and/or stable glassy structure.

A secondary drying step is then followed at full vacuum and formulation temperature between 30° C. and 50° C. The purpose of the secondary drying step is to remove the remaining entrapped or bound moisture and provide a composition that is stable in storage for an extended period of time at ambient temperatures. The secondary drying step may last several hours and its ending point is when the formulation is completely dry and its water activity lower than 0.3 Aw.

The drying methods of the invention results in a biologically active material that is encased within an amorphous glassy matrix, thereby preventing the unfolding of proteins and significantly slowing molecular interactions or cross-reactivity, due to greatly reduced mobility of the compound and other molecules within the amorphous glassy composition. As long as the amorphous solid is at a temperature below its glass transition temperature and the residual moisture remains relatively low (i.e., below Aw of 0.3), the bioactive material remains relatively stable (see FIG. 8). It should be noted that achieving a glassy state is not a prerequisite for long term stability as some bioactive ingredients may fare better in a more crystalline state.

Preparation of Dry Powder

The dried formulation can be used en bloc, cut into desired shapes and sizes, or crushed and milled into a free flowing powder that provides easy downstream processing like wet or dry agglomeration, granulation, tabletting, compaction, pelletization or mixed in food or feed products or any other kind of delivery process. Processes for crushing, milling, grinding or pulverizing are well known in the art. For example, a hammer mill, an air mill, an impact mill, a jet mill, a pin mill, a Wiley mill, or similar milling device can be used. The preferred particle size of the milled particles is less than about 1000 μm and preferably less than 500 μm.

The compositions and methods described herein preserve the biological activity of the encased biologically active material. For example, the compositions are tested for stability by subjecting them at elevated temperature (e.g., 40° C.) and high humidity (e.g. 33% RH) and measuring the biological activity of the formulations. As an example for live probiotic bacteria, results of these studies demonstrate that the bacteria formulated in these formulations are stable for at least 20 days (see FIG. 8). Stability is defined as time for one log CFU/g potency loss. Such formulations are stable even when high concentrations of the biologically active material are used. Thus, these formulations are advantageous in that they may be shipped and stored at temperatures at or above room temperature for long periods of time.

EXAMPLES

The following examples are offered to illustrate, but not to limit the claimed invention.

Example 1

Preparation of Dry and Stable Probiotic Substance

Basic Formulation 75 g of trehalose (Cargill Minneapolis, Minn.) and 22 g of extensively hydrolyzed casein (Marcor, Carlstadt, N.J.) were uniformly mixed with 3 g of sodium alginate (ISP Corp., Wayne, N.J.) in dry form. Fresh concentrate of *Lactobacillus acidophilus* (100 ml containing at least 10% solids, direct from fermentation harvest) was added in a blender and maintained at 35° C. The dry mix of the gum, sugar and hydrolyzed protein was slowly added to the probiotic culture and mixing was carried out at 35° C. for 10 minutes. The viscous slurry was then transferred to a vessel having a perforated bottom and allowed to drip into a bath containing nitrogen. The beads were then removed from the liquid nitrogen and immediately transferred to drying.

Drying of the Frozen Beads of the Basic Formulation

The frozen beads were evenly spread on a tray at a loading capacity of 100 g/sq ft and immediately placed on a shelf in a freeze drier (Model 25 SRC, Virtis, Gardiner, N.Y.). Vacuum pressure was then applied at 1000 mTORR and the solid frozen beads were allowed to purge for 10 minutes. Vacuum was then adjusted to 2700 mTORR and shelf temperature raised to +30° C. These temperature and vacuum pressure were maintained for 3 hours. A secondary drying step was then followed at full vacuum (150-200 mTORR) and shelf temperature raised to 30° C. for additional 2 hours. The formulation was completely dried and its water activity measured by a Hygropalm Aw1 instrument (Rotonic Instrument Corp., Huntington, N.Y.) at Aw=0.23.

Example 2

Stable Dry Composition Containing Probiotic Bacteria *Lactobacillus rhamnosus* LGG.

*Lactobacillus rhamnosus* LGG (500 g frozen concentrate from a commercial source) was thawed at 37° C. in a jacketed dual planetary mixer (DPM, 1 qt, Ross Engineering, Inc. Savannah, Ga.). Two glass forming agents; trehalose (387 g, Cargill Minneapolis, Minn.) and extensively hydrolyzed casein (83 g, Marcor, Carlstadt, N.J.) were homogenously mixed in dry form with two matrix forming agents; sodium alginate (15 g, ISP Corp., Wayne, N.J.) and instant Inulin (25 g, Cargill Minneapolis, Minn.). The dry mix was slowly added to the thawed probiotic bacteria and mixing was carried out at 40 RPM and 37° C. for 10 minutes. The viscosity of the slurry was adjusted to 12,000 Cp by the addition of 50-200 ml of water. The slurry was then transferred to a vessel having a perforated bottom and allowed to drip into a vessel containing liquid nitrogen. The beads were then removed from the liquid nitrogen, placed in sealed aluminum foiled bag and stored in a deep freezer at −80° C. for several weeks.

Figure 6:
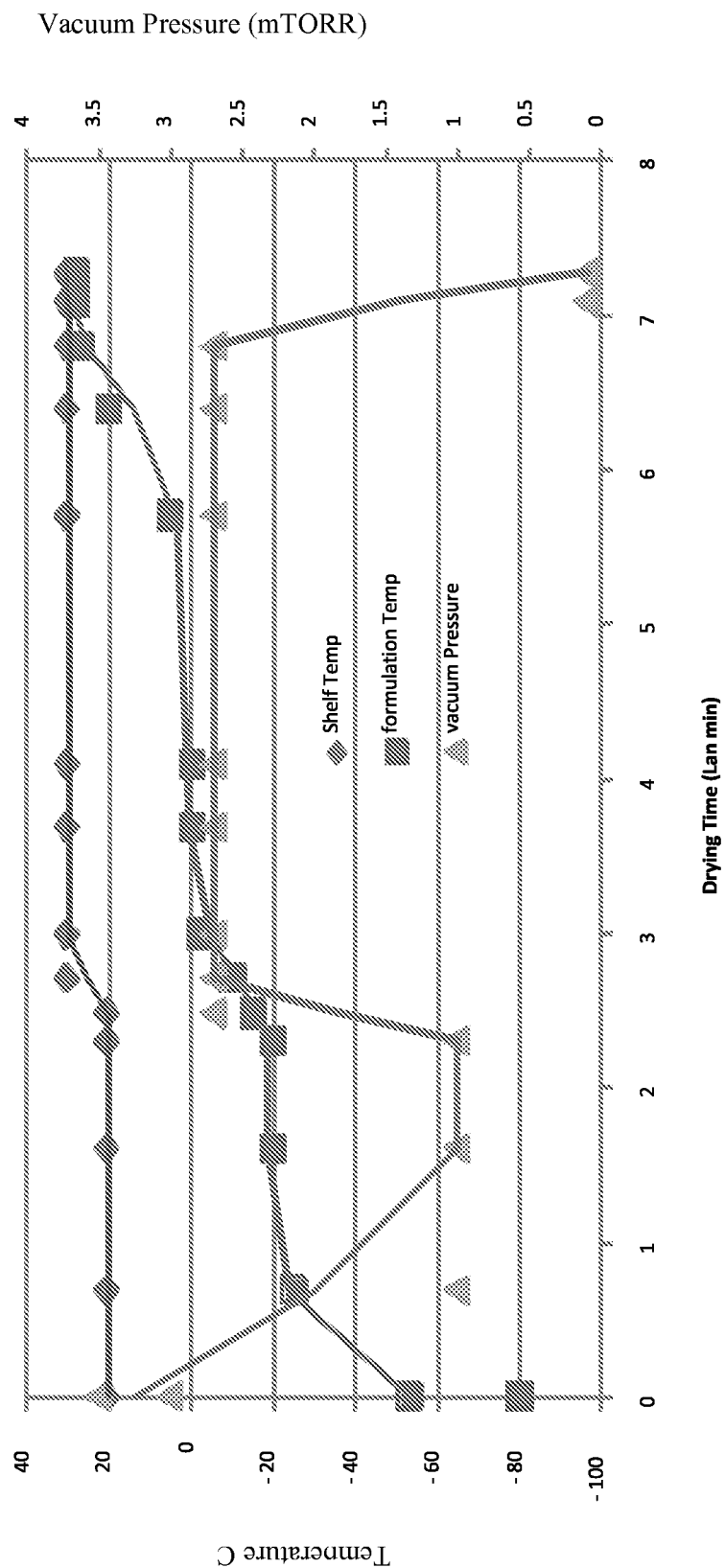
FIG. 6. Drying profile in a freeze drier of the composition according to the method of the invention.

For drying, the frozen beads were evenly spread on trays at a loading capacity ranging from 100 up to 500 g/sq ft and the trays placed on shelves in a freeze drier (Model 25 SRC, Virtis, Gardiner, N.Y.). Vacuum pressure was applied at 1000 mTorr and shelf temperature adjusted to +20° C. The solid frozen beads were allowed to purge for a time period ranging from 1 to 30 minutes. The purging step was followed by a primary drying step after adjusting the vacuum pressure to 2700 mTORR and shelf temperature raised to +30° C. These temperature and vacuum pressure were maintained for 12 hours. A secondary drying step was then followed at full vacuum (150-200 mTORR) and shelf temperature maintained at 30° C. for additional 4 hours. The formulation was completely dried and its water activity measured at 0.23 Aw. FIG. 6 shows the drying profile of the probiotic formulation.

Figure 3:
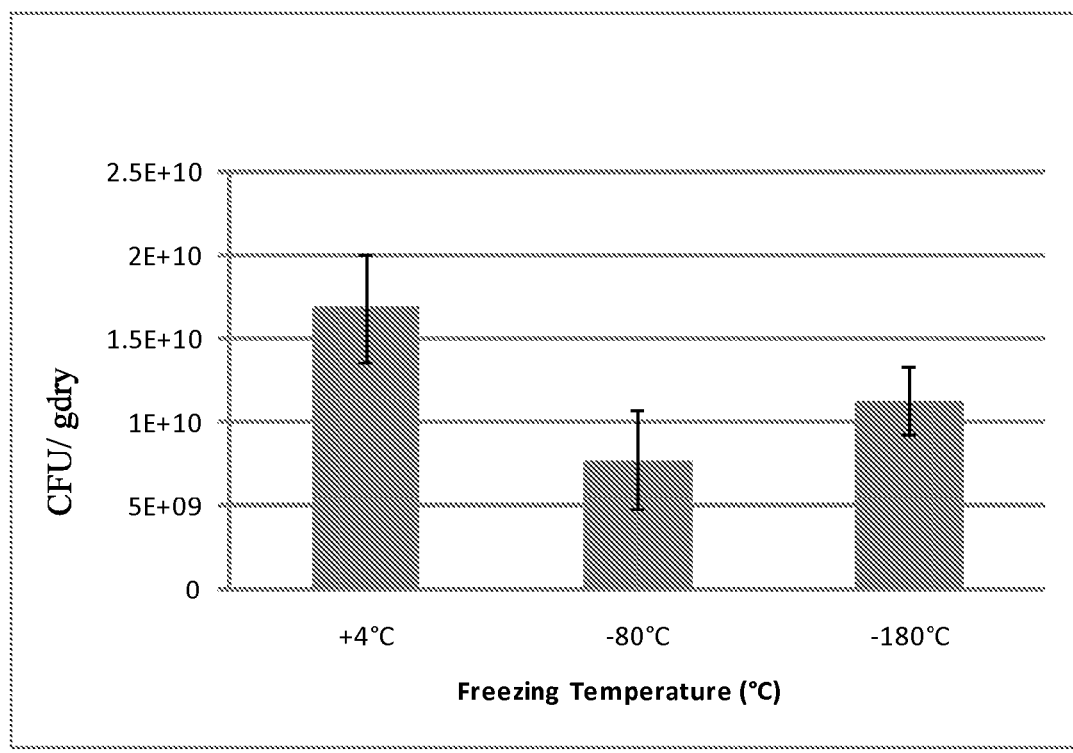
FIG. 3. The effect of freezing temperature of a composition containing L. rhamnosus as frozen solid beads in liquid nitrogen or −80° C. deep freezer and as non-frozen viscous slurry at +4° C. on the bacterial initial CFU counts in the dry composition. Results show only the effect of freezing temperature of the slurry with no additional step of purging before drying.
Figure 4:
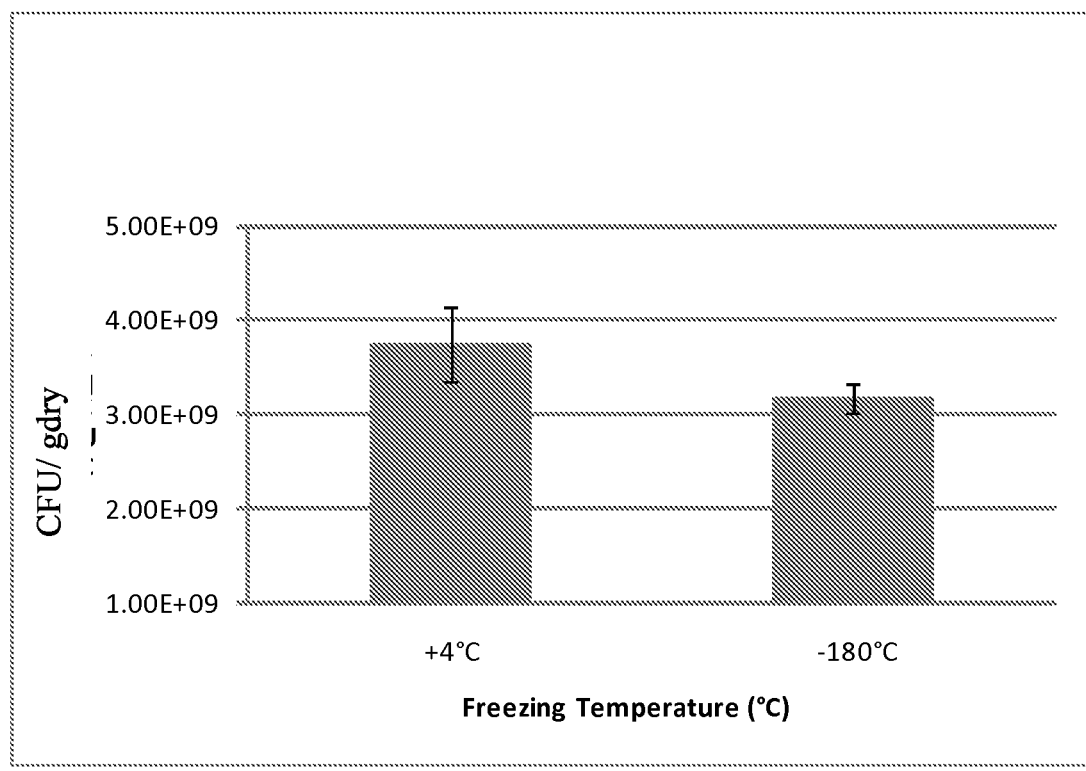
FIG. 4. The effect of freezing temperature of a composition containing *Bifidobacterium animalis* Bb12 as frozen solid beads in liquid nitrogen and as non-frozen viscous slurry at +4° C. on the bacterial initial CFU counts in the dry composition. Results show only the effect of freezing temperature of the slurry with no additional step of purging before drying.

The viability losses after freezing the slurry at different temperatures (+4° C., −80° C. and −180° C.) and after the drying process including preparation of frozen beads, and drying in a freeze-drier are presented in FIGS. 3, 4 and 7. Viability losses for the entire process were generally lower than <1 log depending on the type of bacterial culture (frozen or dry cultures) and on the freezing temperature of the viscous slurry. Results show that snap-freezing of the probiotic bacteria in liquid nitrogen (−180° C.) was a less damaging process than freezing at −80° C.

Figure 5:
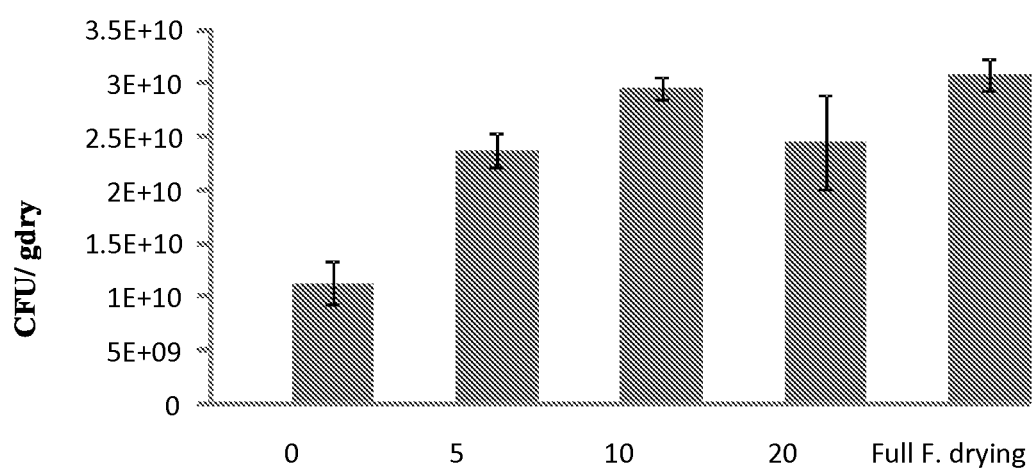
FIG. 5. The effect of purging duration under vacuum of frozen solid beads on initial CFU counts of *L. rhamnosus* in a dry composition.

FIGS. 5 & 8 show the effect of various purging time periods ranging from 0 min (no purging) to 30 min on initial counts of probiotic bacteria in the dry composition and on storage stability under accelerated storage conditions of 40° C. and 33% RH. Results suggest that a longer purging time generally improves the bacterial initial count in the dry formulation but had no effect on storage stability of the probiotic formulation.

Example 3

Trehalose (752 g, Cargill Minneapolis, Minn.), extensively hydrolyzed Pea protein (167 g, Marcor, Carlstadt, N.J.), sodium alginate (30 g, ISP Corp., Wayne, N.J.) and instant Inulin 50 g, Cargill Minneapolis, Minn.) were homogenously blended in dry form. The dry mix was slowly added to 1000 ml hot de-ionized water at 80° C. in a jacketed dual planetary mixer (DPM, 1 qt, Ross Engineering, Inc. Savannah, Ga.) and mixing was carried out at 40 RPM for 10 minutes. The mixture temperature was reduced to 37° C.° C. and 100 g dry powder of *Lactobacillus rhamnosus* LGG obtained from a commercial source was slowly added and mixing continued for 20 minutes. The slurry was then extruded through a 2 mm orifice needle into a bath containing liquid nitrogen. The /strings/beads were then removed from the liquid nitrogen placed in sealed aluminum foiled bag and stored in a deep freezer at −80° C. for several weeks. For drying, the frozen strings/beads were evenly spread on trays at a loading capacity ranging from 100 to 500 g/sq ft and the trays placed on shelves in a freeze drier (Model 25 SRC, Virtis, Gardiner, N.Y.) and dried as described in Example 2. All formulations were contentedly retained within the tray and no splattering or foaming was observed in all loading levels. The formulation was completely dried even at the higher loading capacity and water activity measured at 0.26 Aw and lower for all samples.

Example 4

Preparation of a Hydrogel Formulation Containing Probiotic Bacteria *Bifidobacterium lactis* (Bb12):

Concentrated probiotic slurry of *Bifidobacterium* lactis (Bb12) is prepared according to Example 1. To the basic formulation, 0.5 g of dibasic calcium phosphate is added, followed by 0.5 g of gluconolactone. The slurry was allowed to harden at room temperature over the next 2 hours to form a solid hydrogel. The firm gel was sliced to thin and long threads, using a commercially available slicer/shredder. The thin threads are snap-frozen in liquid nitrogen and loaded on a tray at a loading capacity of 700 g/sq ft and placed in a freeze drier for drying as described in Example 2. The water activity (Aw) of the formulation was 0.05 (Measured by HygroPalm Aw1, Rotonic Huntington, N.Y.). The dry formulation was further ground to fine powder using standard hammer milling equipment and sieved through 50-250 micron screens.

Example 5

Allergen Free Composition Containing Probiotic Bacteria *Lactobacillus acidophilus*.

Trehalose (752 g, Cargill Minneapolis, Minn.), extensively hydrolyzed Pea protein (167 g, Marcor, Carlstadt, N.J.), sodium alginate (30 g, ISP Corp., Wayne, N.J.) and instant Inulin 50 g, Cargill Minneapolis, Minn.) were homogenously blended in dry form. The dry mix was sterilized by slowly adding to 1000 ml hot de-ionized water at 80° C. in a jacketed dual planetary mixer (DPM, 1 qt, Ross Engineering, Inc. Savannah, Ga.) and mixing was carried out at 40 RPM for 10 minutes until smooth and clear slurry is formed. The mixture temperature was reduced to 37° C. and 1000 g frozen beads containing *Lactobacillus acidophilus* obtained from a commercial source was slowly added and mixing continued for 10 minutes. The slurry was then extruded through a 2 mm orifice needle into a bath containing liquid nitrogen. The /strings/beads were then removed from the liquid nitrogen placed in sealed aluminum foiled bag and stored in a deep freezer at −80° C. for several weeks. For drying, the frozen strings/beads were evenly spread on trays at a loading capacity of 1000 g/sq ft and the trays placed on shelves in a freeze drier (Model 25 SRC, Virtis, Gardiner, N.Y.) and dried as described in Example 2. The initial CFU counts of the probiotic bacteria in the dry composition was 10.53 logs/g, and viability loss after 42 days storage under accelerated storage conditions of 40° C. and 33% RH was 0.69 log CFU/g.

Example 6

An Infant Formula Containing the Dry Formulation of the Present Invention:

A stable dry formulation containing *Lactobacillus* GG (Valio Corp, Finland) was prepared according to Example 2 followed by sieving into two particle size groups (above 50 μm and below 150 μm). An infant formula was prepared by mixing 99.9 g of Nutramigen (Mead Johnson; Evansville, Ill.) with 0.1 g of the dry formulation particles in the size range between 50 μm and 150 μm). The final product contains about $10^8$ cfu of *Lactobacillus* GG per 100 g infant formula.

Example 7

A Probiotic Supplement Containing the Stable Dry Formulation of the Present Invention:

A stable dry composition containing *Lactobacillus acidophilus* is formulated into oral dosage forms, such as tablets, caplets, or capsules. Orange flavored tablets containing 99.9 g of a compression agent (dextrose) and 0.1 g of the dry formulation particles in the size range between 50 μm and 150 μm are prepared by direct compression on a rotary machine using a ½" round standard concave tooling. The final product contains about $10^8$ cfu/unit dose. Hardness of the tablets is in the range of 8-10 kp and disintegration times is approximately 20 second. The compressed tablets are packaged into 180 cc HDPE bottles of 100 tablets each and exposed to controlled temperature/humidity of 40° C./33% RH. The product is subjected to monthly microbiological stability testing over a period of 12 months or until a reduction in the assay count below $1 \times 10^6$/unit dose is observed.

Example 8

A Functional Beverage Drink Containing the Stable Dry Formulation of the Present Invention:

A dry mix containing (% by weight) 71% sucrose, 14% maltodextrin, 10% inulin, 2% dextrose, 1% citric acid anhydrous, 0.3% gum acacia, 0.3% flavors, 0.3% Tricalcium phosphate and 0.1% dry probiotic formulation particles (*L. acidophilus*) in the size range between 50 μm and 250 μm is prepared. The final product contains about $10^9$ cfu/unit dose (30 g dry mix). The product is packaged in small aluminum foil bags (30 g unit dose/bag) for drinking by stirring in 340 mil water. The stability of the probiotic bacteria in the beverage dry mix is subjected to monthly microbiological stability testing over a period of 12 months or until a reduction in the assay count below $1 \times 10^7$/unit dose is observed.

Example 9

Preparation of Probiotic Pet Food:

A commercially available pelleted pet food for dogs is dried in a convection oven to a water activity of 0.1, and then coated with the stable probiotic dry formulation prepared as described in Example 3. The dry pellets are sprayed with about 5% of fat-based moisture barrier (a mixture of 40% chicken fat, 40% cocoa butter and 20% beeswax), mixed in a drum tumbler with the dry powder formulation (usually 0.1-0.5% of total pet food that provides a dosage of $10.^{sup}8$ CFU/g), and finally sprayed with additional coat of the fat-based moisture barrier. The total amount of coating is about 15% (of the pet food). Coating time is about 30 min.

Example 10

Preparation of Fish Feed with Several Probiotic Microorganisms:

Pelleted feed for fish according to the present invention is prepared with a mixture of several probiotics. A stable dry probiotic formulation containing a mixture of *L. rhamnosus, L. acidophilus* and *Bifidobacterium* lactis is prepared as described in Example 1. A commercially available starter feed for salmon (Zeigler Bros., Gardners, Pa.) is first dried in a convection oven to a water activity of 0.1, and then coated with the probiotics formulation in a drum tumbler. The pellets (1000 g) are first sprayed with about 5% by weight of fat-based moisture barrier (a mixture of 40% fish oil, 40% cocoa butter and 20% beeswax), then mixed with 1 g of the stable dry probiotic formulation (to attain a dosage of $10^7$ cfu/g feed), and finally sprayed with additional coat of the fat-based moisture barrier. The total amount of coating is about 10% (of the fish feed).

Example 11

Stable Dry Powder Containing an Enzyme:

A hydrogel formula containing 40 weight percent of Savinase (Novozymes, Denmark) is prepared by mixing 600 g of the formulation described in Example 4 and 400 g of savinase in 1000 g of water solution. The shredded hydrogel formulation is snap-frozen in liquid nitrogen and dried in a vacuum oven at a formulation drying temperature of 50° C. For determination of loading and storage stability of the dried formula: a dry sample is accurately weighed (<100 mg) in a microcentrifuge tube. 200 μl of dimethyl sulfoxide (DMSO) is added. The formulation is dissolved in the DMSO buffer by vortexing. To this sample, 0.8 ml of a solution containing 0.05 N NaOH, 0.5% SDS and 0.075 M Citric acid (trisodium salt) is added. The tubes are sonicated for 10 min at 45° C., followed by a brief centrifugation at 5,000 rpm for 10 min. Aliquots of the clear DMSO/NaOH/SDS/Citrate solution are taken into wells of a microplate and analyzed for protein content using the Bradford assay method. The storage stability of the stable enzyme formulation is significantly higher than a dry enzyme without the formulation of the present invention.

Example 12

Stable Dry Powder Containing Vitamin A:

A formulation containing 30 weight percent of Vitamin A is prepared by mixing 320 g instant inulin, 320 g maltodextrin DE-1 (Tate&Lyle, London, UK), 50 g sodium carboxymethylcelullose (Ashland Aqualon Functional Ingredients, Wilmington, Del.), 10 g sodium ascorbate and 300 g of vitamin A crystalline (BASF Corp., Florham Park, N.J.) in 1000 g water. The wet formulation is spray-dried in a Mobile-Minor spray drier (GEA Process Engineering Inc., Columbia Md.) at inlet and outlet temperature of 180° C. and 80° C., respectively or snap-frozen in liquid nitrogen, then spread on trays at a loading capacity of 1000 g/sq ft and dried as described in Example 2. The vitamin-A composition is stable (>80%) at 40° C. and 75% RH for 3 months.

Example 13

Preparation of Carotenes in a Protected Formulation Having Enhanced Bioavailability:

A formulation that protects and enhances the bioavailability of carotenes that would otherwise be subject to oxidation by other ingredients in a feed during storage or after feeding an organism is prepared according to the formulation and the method of the present invention. A formulation containing 6 g of water soluble chitosan (LSK BioPartners, Inc. Salt Lake City, Utah) is dissolved in 200 g water. To this solution is added 90 g of natural astaxanthin (Naturose™, Cyanotech Corp., Kailua-Kona, Hi.) and the slurry is atomized or extruded into a bath containing 5% sodium tripoliphosphate. The hydrogeled microparticles or strings are allowed to harden at room temperature over 4 hours. The particles are removed from the cross-linking bath, washed with water and mixed with a dry blend of 90 g sucrose and 10 g extensively hydrolyzed casein. The sugar/protein loaded particles are snap-frozen and immediately placed on trays at 500 g/sq ft and lyophilized in a freeze dryer until water activity reduced to less than 0.3. The dry formulation is further milled to the desired size distribution and packaged.

Example 14

Preparation of Invasive Species Bait

Pelleted bait for specifically targeted invasive species is prepared according to the present invention. 200 g of a formulation containing a pesticide as described in Example 1 is prepared and added to 200 gm of water. To this solution is added 90 gm of Rotenone and 0.5 gm of calcium phosphate dibasic, followed by 0.5 gm of gluconolactone. The slurry is allowed to harden at room temperature over 2 hours. The firm gel is sliced to thin and long threads through a slicer/shredder. The thin threads are loaded on a tray and placed in a freeze dryer. Shelf temperature is set at −30° C. and the formulation allowed freezing before full vacuum is applied and shelf temperature rose to +60° C. for over-night drying. The dry formulation is ground to the appropriate size distribution for the bait size specification for the specific species targeted.

Example 15

Preparation of a Protected Pesticide in a Water Insoluble Formulation:

A protected granular formulation of a pesticide that would otherwise be subject to decomposition by other ingredients in a formulation during storage or after application in the environment is prepared with the formulation and the method of the present invention. A formulation containing 6 g of pectin and 102 g sucrose is added to 200 g water. To this solution is added 90 g of a dry formulation of a sensitive pesticide and a mixture containing 1.5 g of calcium phosphate dibasic and 0.5 g of calcium chloride, followed by 0.85 g of gluconolactone. The slurry is allowed to harden at room temperature over 4 hours, and then sliced to thin, long threads through a slicer/shredder. The thin threads are loaded on trays and dried in a freeze dryer to reach a water activity of 0.1. The dry formulation is further milled to the desired size distribution and packaged.

Example 16

Preparation of a Protected Plant Probiotic Formulation:

A biological control agent such as Rhizobacteria is prepared in dry composition according to Example 4. The effectiveness of the dry Rhizobacteria composition is evaluated on lettuce growth under gnotobiotic conditions. Doses of 100 mg of Rhizobacteria dry composition per plant are inoculated into jars with sand and planted with pre-germinated (24 h) lettuce seedlings. A nutrient dose of 5 ml of sterilized Hoagland solution is applied to the plants in the jar. Jars are arranged randomly in growth chamber maintained at 28° C. with 12 h photoperiod. During every 7 days interval after inoculation, plants and adhering sand are carefully removed from the jars. Roots are washed in sterile phosphate buffer (pH 7.0), and measurement of root length is recorded.

Reference

The following references and all references cited herein are hereby incorporated by reference herein for all purposes.

U.S. Patent References:

U.S. Pat. No. 6,190,701 Composition and method for stable injectable liquids, Mar. 1999, Roser et al.

U.S. Pat. No. 6,964,771 Method for stably incorporating substances within dry, foamed glass matrices, Sep. 1997, Roser et al.

U.S. Pat. No. 5,766,520 Preservation by formulation formation, Jun. 1998, Bronshtein U.S. Pat. No. 6,534,087 Process for preparing a pharmaceutical composition, Jun. 2001, Busson and Schroeder.

U.S. Pat. No. 6,884,866 Bulk drying and the effects of inducing bubble nucleation, Apr. 2005, Bronshtein.

U.S. Pat. No. 7,153,472 Preservation and formulation of bioactive materials for storage and delivery in hydrophobic carriers, Dec. 2006, Bronshtein 20080229609 Preservation by Vaporization, Jun. 2005, Bronshtein U.S. Pat. No. 6,306,345 Industrial scale barrier technology for preservation of sensitive biological materials at ambient temperatures, Oct. 2001, Bronshtein et al.

U.S. Pat. No. 7,381,425 Preservation of bioactive materials by freeze dried foam, Sep. 2006, Truong-le, Vu.

Other References:

Morgan, C. A., Herman, N., White, P. A., Vesey, G. 2006. Preservation of micro-organisms by drying; a review. *J. Microbiol. Methods.* 66(2):183-93.

Capela, P., Hay, T. K. C., & Shah, N. P. 2006. Effect of cryoprotectants, prebiotics and microencapsulation on survival of probiotic organisms in yoghurt and freeze-dried yoghurt. *Food Research International,* 39(3) 203-211).

Annear, 1962. The Preservation of *Leptospires* by Drying From the Liquid State, *J. Gen. Microbiol.,* 27:341-343.

Crowe, J. F., Carpenter, J. F. and Crowe, L. M. 1998. THE ROLE OF VITRIFICATION IN ANHYDROBIOSIS. *Annu. Rev. Physiol.* 60:73-103.

That which is claimed is:

1. A method for preparing a dry glassy composition without boiling or foaming, said method comprising:
   (a) combining a bioactive material, a matrix forming agent and two glass forming agents in an aqueous solvent to form a viscous slurry;
   (b) snap-freezing the slurry in liquid nitrogen to form solid frozen particles in a form of beads, droplets or strings;
   (c) primary drying the frozen particles by evaporation, under vacuum, and at a temperature above the freezing point of the frozen particles, wherein the pressure is greater than 2,000 mTORR, wherein the temperature of the particles is greater than −10° C., whereby a primarily dried formulation is formed; and
   (d) secondary drying the primarily dried formulation at full vacuum and a temperature of 20° C. or higher for a time sufficient to reduce the water activity of the primarily dried formulation to Aw −0.3 or lower, whereby the dry glassy composition is prepared.

2. The method of claim 1, wherein the temperature in the secondary drying step is from 20° C. to 70.

3. The method of claim 1, wherein the temperature or vacuum is increased during the secondary drying step.

4. The method of claim 1, further comprising cutting, crushing, milling or pulverizing the composition into a free flowing powder.

5. The method of claim 4, wherein particle size of the powder is less than about 1000 μm.

6. The method of claim 1, further comprising administering the composition to an animal or plant as a reconstituted liquid or as a ground powder in a food or feed product.

7. The method of claim 1, further comprising
   (a) mixing the composition with a component selected from the group consisting of infant formula, functional beverages, and pet food; and
   (b) administering the mixture from step (a) to a human infant, a human adult, an animal or a plant.

8. A composition prepared according to the method of claim 1.

9. A composition prepared according to the method of claim 2.

10. The method of claim 1, wherein the pressure in the primary drying step is between 2,000 mTORR and 10,000 mTORR.

11. The method of claim 1, wherein the pressure in the primary drying step is between 2,000 mTORR and 4,000 mTORR.

12. The method of claim 1, wherein the temperature in the primary drying step is between −5° C. and +5° C.

13. A dry glassy composition, comprising a bioactive material, at least one matrix forming agent and at least two glass forming agents, wherein the composition is prepared by the method of claim 1.

14. The composition of claim 1, wherein the composition comprises total solids ranging from 30 weight percent to 70 weight percent.

15. The composition of claim 1, wherein the bioactive material comprises a cell, a microbe, a virus, a cell culture, a bacteria, a probiotic bacteria, a plant and soil probiotic bacteria, a yeast, a protein, a recombinant protein, an enzyme, a peptide, a hormone, a vaccine, a drug, an antibiotic, a vitamin, a carotenoid, a mineral, a microbiocide, a fungicide, a herbicide, an insecticide or a spermicide.

16. The composition according to claim 1, wherein the matrix forming agent is a polysaccharide selected from the group consisting of: cellulose acetate phthalate (CAP), carboxy-methyl-cellulose, pectin, sodium alginate, salts of alginic acid, hydroxyl propyl methyl cellulose (HPMC), methyl cellulose, carrageenan, guar gum, gum acacia, xanthan gum, locust bean gum, chitosan and chitosan derivatives, starches and modified starches, cyclodextrins, inulin, maltodextrins, dextrans, and combinations thereof.

17. The composition of claim 1, wherein the matrix forming agent is present in the composition in an amount ranging from 1 weight percent to 20 weight percent.

18. The composition according to claim 1, wherein the glass forming agents are readily soluble in a solution, do not thicken or polymerize upon contact with water, and do not form crystals during drying.

19. The composition according to claim 1, wherein each of the glass forming agents is selected from the group consisting of proteins, carbohydrates, amino acids, methylamine, polyol, propylene glycol, polyethylene glycol, surfactants, phospholipids, and combinations thereof.

20. The composition of claim 1, wherein the glass forming agents are present in the composition in an amount ranging from 1 weight percent to 80 weight percent.

* * * * *

UNITED STATES PATENT AND TRADEMARK OFFICE
CERTIFICATE OF CORRECTION

PATENT NO. : 8,834,951 B2
APPLICATION NO. : 13/378106
DATED : September 16, 2014
INVENTOR(S) : Moti Harel, Roger Drewes and January Scarbrough It is certified that error appears in the above-identified patent and that said Letters Patent is hereby corrected as shown below:

In the Claims

At Column 21, line 31, "of claim 1," should read -- of claim 13, --;

At Column 22, line 1, "of claim 1," should read -- of claim 13, --;

At Column 22, line 8, "to claim 1," should read -- to claim 13, --;

At Column 22, line 17, "of claim 1," should read -- of claim 13, --;

At Column 22, line 20, "to claim 1," should read -- to claim 13, --;

At Column 22, line 24, "to claim 1," should read -- to claim 13, --; and

At Column 22, line 29, "of claim 1," should read -- of claim 13, --.

Signed and Sealed this
Twelfth Day of May, 2015

Michelle K. Lee
*Director of the United States Patent and Trademark Office*